United States Patent [19]
Manning et al.

[11] Patent Number: 5,935,105
[45] Date of Patent: *Aug. 10, 1999

[54] INTRAVENOUS-LINE AIR-ELIMINATION SYSTEM

[75] Inventors: Robert Manning, Pembroke; William T. Larkins, Manchester, both of N.H.; Philip Houle, Palo Alto, Calif.; Dean L. Kamen, Bedford; Valentine Faust, Bow, both of N.H.

[73] Assignee: Deka Products Limited Partnership, Manchester, N.H.

[ * ] Notice: This patent is subject to a terminal disclaimer.

[21] Appl. No.: 08/961,410

[22] Filed: Oct. 30, 1997

Related U.S. Application Data

[63] Continuation of application No. 08/478,065, Jun. 7, 1995, Pat. No. 5,755,683, application No. 08/472,212, Jun. 7, 1995, Pat. No. 5,772,637, application No. 08/477,380, Jun. 7, 1995, Pat. No. 5,641,892, and application No. 08/481,606, Jun. 7, 1995, Pat. No. 5,713,865, which is a continuation-in-part of application No. 08/306,459, Sep. 15, 1994, Pat. No. 5,533,389, which is a division of application No. 07/792,877, Nov. 15, 1991, Pat. No. 5,349,852.

[51] Int. Cl.$^6$ .................................................. A61M 1/00
[52] U.S. Cl. ............................................................. 604/122
[58] Field of Search .................................. 604/122, 118, 604/131, 149, 28, 30, 31, 65, 123, 151, 153

[56] References Cited

U.S. PATENT DOCUMENTS

| | | |
|---|---|---|
| 2,252,687 | 8/1941 | Bassett . |
| 2,835,252 | 5/1958 | Mauchel . |
| 3,007,416 | 11/1961 | Childs . |
| 3,042,038 | 7/1962 | Beacham ................................... 137/74 |
| 3,677,242 | 7/1972 | Shaye .................................. 128/214 C |
| 4,391,599 | 7/1983 | Jenkins ..................................... 604/118 |
| 4,573,883 | 3/1986 | Noon et al. .............................. 417/394 |
| 4,634,430 | 1/1987 | Polaschegg ............................. 604/141 |
| 4,661,097 | 4/1987 | Fischell et al. .......................... 604/123 |
| 4,734,269 | 3/1988 | Clarke et al. ............................ 422/310 |
| 4,764,166 | 8/1988 | Spani ......................................... 604/65 |
| 4,826,482 | 5/1989 | Kamen ...................................... 604/67 |
| 4,874,359 | 10/1989 | White et al. ................................. 604/4 |
| 5,061,241 | 10/1991 | Stephens, Jr. et al. .................. 604/114 |
| 5,211,201 | 5/1993 | Kamen et al. ............................... 137/1 |
| 5,241,985 | 9/1993 | Faust et al. ......................... 137/505.13 |
| 5,308,333 | 5/1994 | Skakoon .................................. 604/126 |
| 5,713,865 | 2/1998 | Manning et al. ........................ 604/122 |

FOREIGN PATENT DOCUMENTS

| | | |
|---|---|---|
| 0 227 885 | 7/1986 | European Pat. Off. . |
| 0 293 592 | 4/1988 | European Pat. Off. . |
| 247 607 A1 | 7/1987 | Germany . |
| 2093700 | 8/1981 | United Kingdom . |
| WO 91/13677 | 9/1991 | WIPO . |

*Primary Examiner*—Manuel Mendez
*Attorney, Agent, or Firm*—Bromberg & Sunstein LLP

[57] ABSTRACT

An air elimination system is provided for an intravenous fluid delivery system for intravenous injection of fluid into a patient. An air-detection apparatus is disposed in an intravenous fluid line. At the top end of the line is attached a chamber where air may be separated from the fluid. The separation chamber may be a drip chamber, a metering chamber or the intravenous supply. When air is detected, a valve or valves are switched, so that the intravenous fluid is prevented from flowing to the patient, and so that, when a pump is turned on, the fluid is pumped to the separation chamber. In a preferred embodiment, the volume of pump's fluid capacity is greater than the volume of the fluid capacity of the intravenous line between the pump and the separation chamber so that the pump can force air back up the intravenous line all the way to the separation chamber.

8 Claims, 8 Drawing Sheets

INTRAVENOUS-LINE AIR-ELIMINATION SYSTEM

RELATED APPLICATIONS

This application is a continuation of application Ser. No. 08/481,606 filed Jun. 7, 1995, now U.S. Pat. No. 5,713,865, which is a continuation-in-part of application Ser. No. 08/306,459 filed Sep. 15, 1994, now issued as U.S. Pat. No. 5,533,389, which is a divisional of application Ser. No. 07/792,877 filed Nov. 15, 1991 for an invention by Kamen, Seale, Briggs and Arnold, now issued as U.S. Pat. No. 5,349,852, and which was filed concurrently with and incorporated by reference application Ser. No. 07/792,483, for an invention by Kamen and Faust now issued as U.S. Pat. No. 5,211,201. This application is also a continuation of applications Ser. No. 08/478,065 filed Jun. 7, 1995, now U.S. Pat. No. 5,755,683 Ser. No. 08/472,212 filed Jun. 7, 1995, now U.S. Pat. No. 5,772,637, and Ser. No. 08/477,380 filed Jun. 7, 1995, now U.S. Pat. No. 5,641,892. All of these related applications are incorporated herein by reference.

TECHNICAL FIELD

The present invention relates to apparatus and methods for eliminating air bubbles from intravenous lines.

BACKGROUND ART

It has been the object of many prior-art devices to detect the presence of air bubbles in an intravenous line. Such devices would normally set off an alarm to alert the appropriate medical personnel, who would then lightly rap the line to urge the bubbles up the line away from the patient. It is a tedious procedure to urge all the bubbles all the way up the IV line to the IV fluid reservoir. It is even more difficult to remove bubbles located downstream of a pump. Since, in an IV line that is not being pumped at high pressure, small bubbles usually do not pose much danger to the patient, busy medical personnel rarely go through the trouble of urging the bubbles all the way up the line. Consequently, the bubbles quickly move back down the line and are detected again, thereby setting off the alarm again. Thus, without an easy way of removing air from the IV line, the prior-art air-detection systems are more of a nuisance than an aid.

At least one medical apparatus in the prior art includes a line for recycling air removed from fluid back to a reservoir without opening the fluid flow loop to the environment. U.S. Pat. No. 4,874,359 to White et al. discloses a modular, power augmented medical infusion apparatus to provide rapid transfusion of relatively large quantities of blood, blood components, colloid and fluids to patients who require large quantities of these blood components to be rapidly transferred. The major components comprise a pair of filtered cardiotomy reservoirs, an air embolus sensor, a modular double roller pump, a heat exchanger, a bubble trap-filter and disposable fluid conduits. The bubble trap-filter is located in the distal most location of the recirculating loop just upstream of the Y-connector to the patient and the air sensor just downstream of the cardiotomy reservoir in the proximal location of the recirculating loop. Blood is circulated rapidly from the cardiotomy reservoir through the heat exchanger wherein it is heated or cooled as needed and through an air bubble trap filter having a nominal filtering capability of 33 microns. A secondary path from the filter is provided to permit the air trapped in the filter to be recycled to the reservoir without opening the infuser loop to the environment. The air bubble detection system uses an infrared analyzer as a sensor. The detection system is configured to stop the pump and sound an audible alarm. It does not control the recycling of trapped air from the filter.

U.S. Pat. No. 4,764,166 to Spani discloses an ultrasonic device for detecting the presence of air in the fluid line of an IV infusion device comprises a transmitter and a receiver which are positioned to pinchingly engage a portion of the fluid line therebetween. Both the transmitter and receiver have convex-shaped lenses which contact and cause a slight indentation of the tube for enhanced coupling therebetween.

U.S. Pat. No. 4,734,269 to Clarke et al. discloses a venous reservoir bag with an integral high-efficiency bubble removal system. The system includes a container having an inlet for a fluid which includes liquid and gas bubbles, an outlet and upstream and downstream vents. A filter element is provided in the container between the inlet and the outlet. The filter element permits the passage of the liquid and inhibits the passage of the gas bubbles. The filter element is between the upstream and downstream vents so that gas bubbles can be vented through the upstream vent, and any gas bubbles downstream of the filter element can be vented through the downstream vent.

U.S. Pat. No. 4,661,097 to Fischell et al. discloses a method for removing gas bubbles from the fluid handling system of a medication infusion system implanted in a patient. Specifically, Fischell discloses a method for removing fluid and/or gas bubbles from a fluid reservoir and pumping chamber by applying a vacuum or negative pressure to the inlet filter, thereby drawing gas bubbles from the pumping chamber. The invention utilizes a fluid pump of a single valve positive displacement design with the pump chamber in fluid communication with the fluid reservoir.

None of the above references disclose a system that, on detection of air in the intravenous fluid, shuts off flow of the fluid to the patient and forces the fluid towards the intravenous-fluid supply.

SUMMARY OF THE INVENTION

The present invention provides an air elimination system in an intravenous-fluid delivery system that intravenously injects fluid into a patient. The intravenous-fluid delivery system receives a disposable cassette disposed in the intravenous line. The intravenous-fluid delivery system includes a control unit having a housing, which has a receiving surface against which the cassette is placed. The invention may include an intravenous (IV) line with a chamber disposed therein where air may separate from the fluid. Also disposed in the IV line is an air detector for detecting air in the fluid and emitting a fault-condition signal, when an air bubble of a certain size is detected, or alternatively when any air bubble is detected. The IV line has a first portion between the separation chamber and the air detector, and a second portion between the air-detection means and the patient. A valve is disposed in the IV line's second portion, for permitting or preventing flow to the patient. A pump is used to urge fluid towards the separation chamber upon activation. A controller, in communication with the air detector, controls the valve and the pump. In the event of a fault-condition signal, the controller sets the valve to prevent flow to the patient and activates the pump so as to move air and fluid from the air detector to the separation chamber. Otherwise, the pump and the valve may be used to permit flow to the patient or to pump fluid to the patient.

In one embodiment, a return line connects the chamber to a point in the IV line downstream of the air detector. A pair of valves, one being disposed in the IV line and the other in the return line—or alternatively a single shunt valve—are employed to permit flow either (i) through the return line or (ii) to the patient. When there is a fault condition, the pump urges fluid containing the air towards the separation chamber, preferably through the return line. Alternatively, fluid may flow from the fluid source through the return line to a point below the detected air, so as to force the air up through the first portion of IV line.

In a preferred embodiment, a return line is not necessary. The air is forced up the first portion of the IV line by a reservoir of fluid located at or below where the air is detected. By configuring the volume of this reservoir to be greater than the volume of the lumen of the IV line's first portion, the air can be forced up to the separation chamber. If there is a great deal of air in the line, several iterations of this air-purging process may be necessary to eliminate all of the air.

The control unit, of course, requires a power supply. The control unit may use alternative power supplies and may involve communication amongst a plurality of control units to control a plurality of lines leading to the same patient. In one preferred embodiment, the control unit includes AC means for receiving AC power from a wall outlet and converting the AC power to DC power; the AC means is connected to the control unit housing by a first cord for carrying DC power. The control unit further includes DC means for providing power from another control unit instead of a wall outlet. The DC means permits receiving DC power from a second control unit mounted on the same pole, wherein the second control unit is connected to a wall outlet; the DC means includes a second cord for carrying DC power. The second cord may include additional wires for carrying electrical signals between the control units. The control unit also preferably includes (i) internal-battery means for providing DC power when the AC means is disconnected from the wall outlet, the internal battery means being located inside the housing, and (ii) external-battery-receiving means for permitting an external battery pack to be connected to the housing's exterior to provide power to the control unit in lieu of AC power from a wall outlet and from the internal-battery means.

DETAILED DESCRIPTION OF SPECIFIC EMBODIMENTS

The invention provides an apparatus and method for eliminating air from intravenous fluid delivery systems. In a preferred embodiment, an acoustic sensor is utilized to control the operation of a valve located downstream of the IV pump so that when air bubbles are detected, an isolation valve is closed to shut off the flow of IV fluid to the patient and the fluid containing the air is returned the metering chamber, the drip chamber or the intravenous-fluid source.

A system according to the present invention may include an apparatus that accurately dispenses IV fluid to the patient, using sound waves both to measure fluid flow and to detect the presence of air in the IV fluid. The apparatus includes a return line that carries fluid back to the metering chamber if and when the apparatus detects air in the fluid. Although almost any air-detection system may be used, it is intended that a preferred embodiment of the present invention be used with an apparatus that uses sound waves to measure flow and uses sound waves to detect air, such as that disclosed in the above-referenced U.S. Pat. No. 5,349,852, or the above-referenced patent application Ser. No. 08/477,380 filed Jun. 7, 1995.

Figure 1:
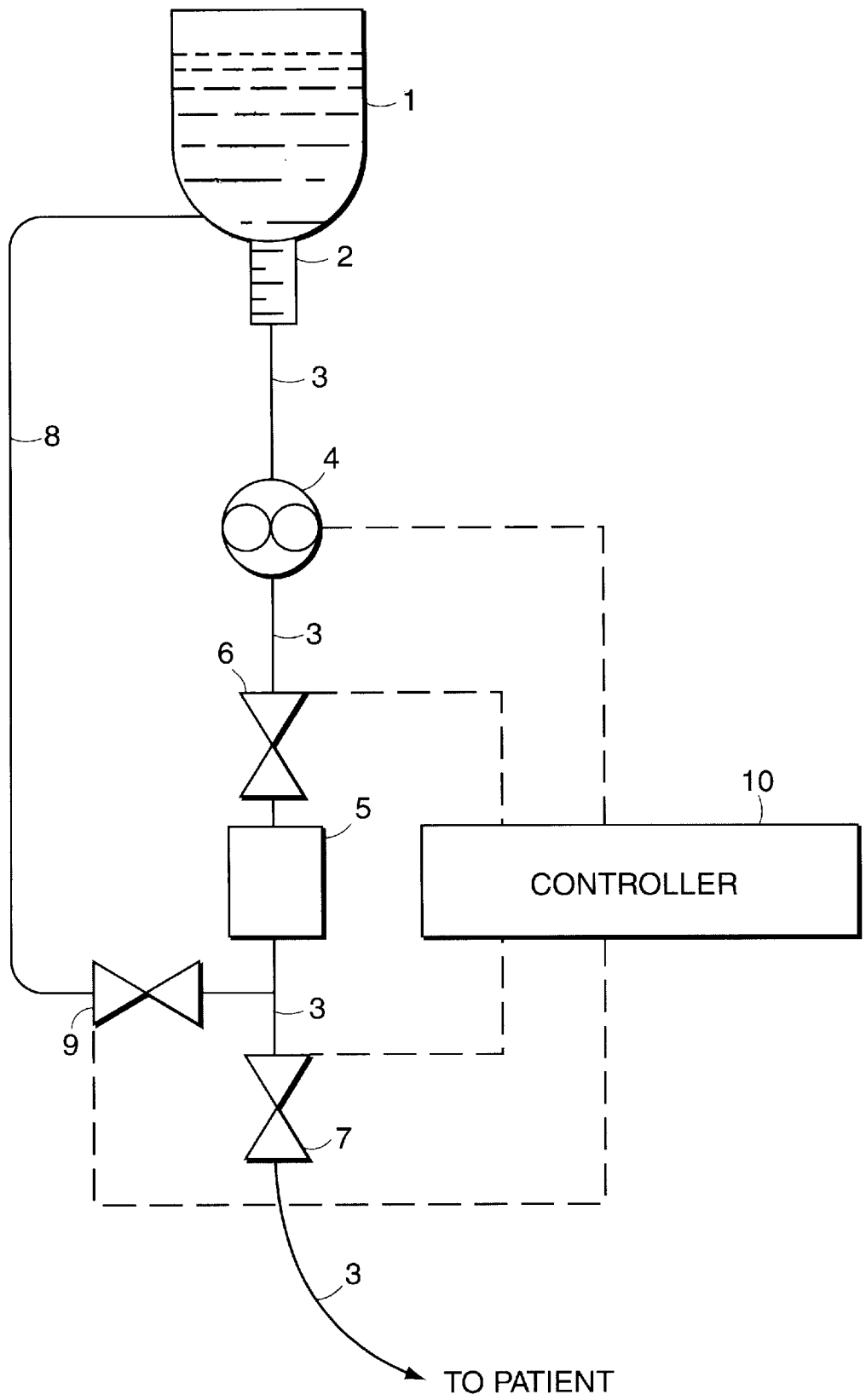
FIG. 1 is a general view of an embodiment of an air elimination system according to the present invention.

FIG. 1 shows an intravenous-fluid bag (or bottle) 1 and metering chamber 2, from which an IV line 3 provides fluid to the patient. Disposed in the line is a pump 4, an apparatus for detecting air and preferably for measuring flow rate 5, and a valve 7. The air-detection/fluid-measurement apparatus 5 is downstream of the pump 4, and the valve 7 is located downstream of the apparatus 5. One end of the return line 8 is connected to the IV line 3 between the air-detection apparatus 5 and valve 7; its other end is connected to the metering chamber 2. Another valve, a purge valve 9, is located in the return line.

When air, or a certain amount of air, is detected, valve 7 is closed and purge valve 9 is opened. The pump 4 is turned on, forcing the fluid and the air bubbles in the air-detection apparatus 5 to return to the metering chamber 2. The metering chamber 2 allows the air bubbles to separate from the IV fluid. Other devices, such as a drip chamber, or even the IV bag (or bottle) 1, may be used to allow the air to separate from the fluid. When the air has been eliminated from the apparatus, purge valve 9 may be closed and the IV system may return to its normal pumping mode. A digital controller 10 receives information from the detector 5 regarding the presence of air, controls the opening and closing of valves 7 and 9, and controls the pump 4. The air detector 5, as well as the controller 10, may be made a part of an IV fluid control system, such as that disclosed in U.S. Pat. Nos. 5,349,852 or 4,976,162. The system disclosed in U.S. Pat. No. 4,976,162 uses two valves, A and B, for isolating a portion of the IV fluid during a volume measurement cycle, and these are shown as valves 6 and 7 in FIG. 1; the valve B of U.S. Pat. No. 4,976,162 is used as valve 7 of the present invention. Valve 6 of the present invention corresponds to valve A.

Figure 2:
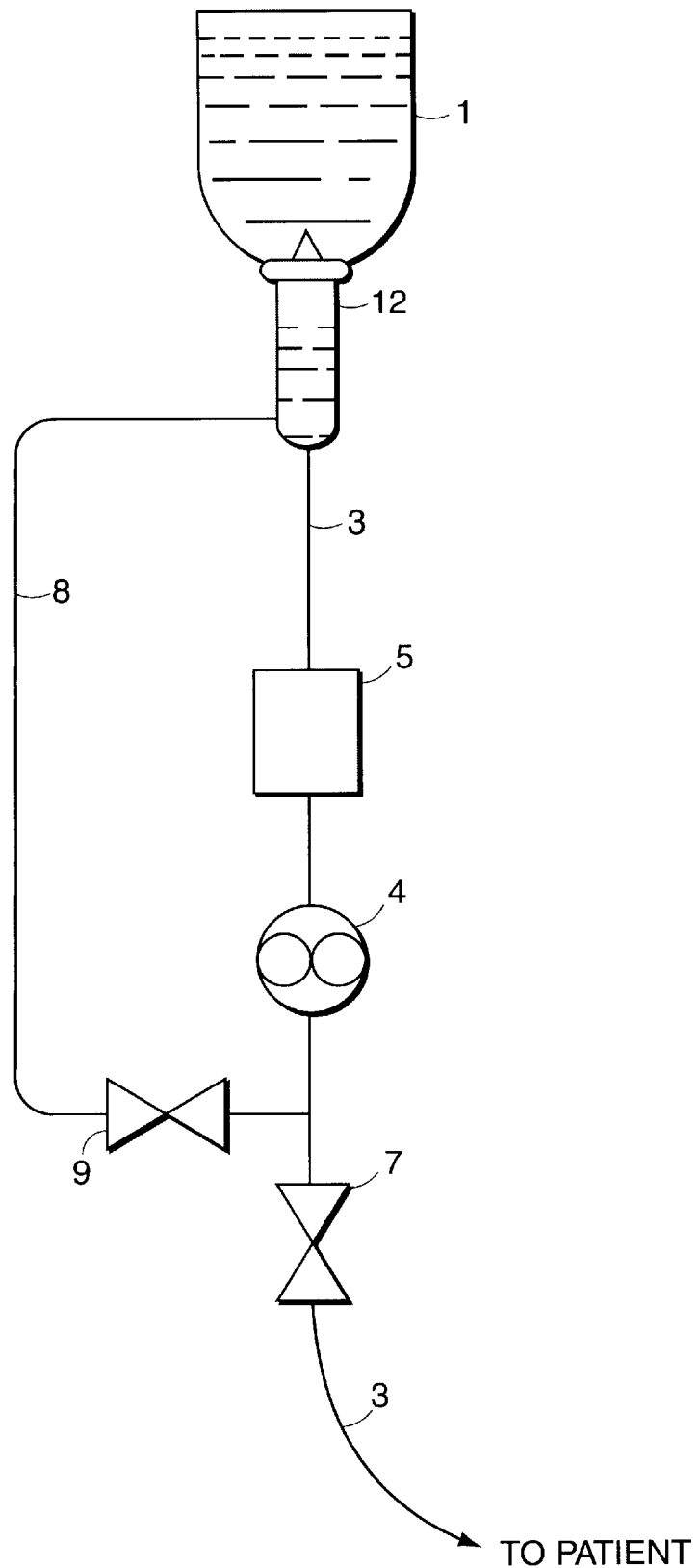
FIGS. 2 and 3 show alternative embodiments of the air elimination systems according to the present invention.
Figure 3:
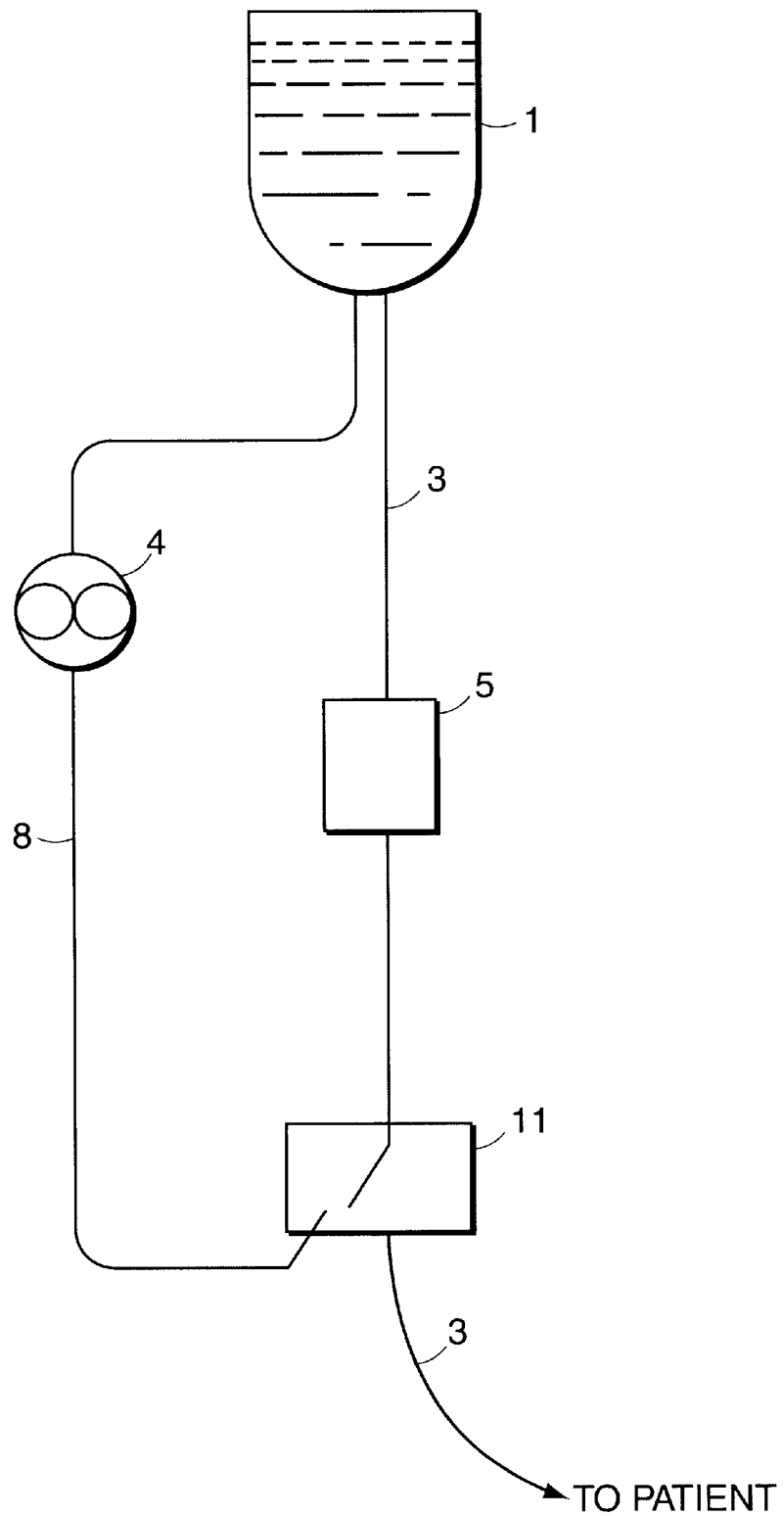

In another embodiment of the present invention, the pump 4 may be located in the IV line 3 downstream of the air detector 5 but upstream of the point where the return line 8 is connected to the IV line 3, as shown in FIG. 2. The system shown in FIG. 2 has the return line returning to a simple drip chamber 12 instead of a metering chamber. FIG. 3 shows another embodiment, wherein the pump 4 is disposed in the return line 8 and the return line 8 returns fluid to the reservoir 1, and wherein a single shunt valve 11 is used instead of two separate valves 7 and 9. A disadvantage of the FIG. 3 embodiment is that the pump 4 cannot, of course, be used to pump IV fluid to the patient.

In all the foregoing embodiments it is preferred that, when air is detected, the fluid and the air bubbles from the detector 5 is pumped back to the reservoir, metering chamber or drip chamber through the return line 8. In another embodiment the pump 4 may be reversed so that the IV fluid and air bubbles in the air detector 5 are forced up the IV line 3 back to the reservoir, with fluid in the return line 8 replenishing that which has been pumped out of the detector 5. The disadvantage of such an embodiment is that the return line 8 must be attached to the reservoir, metering chamber or drip chamber below the waterline; otherwise the pump will draw air into the return line instead of fluid, and, if the pumping continues long enough, this air will move into the IV line 3 and the air detector 5.

A disposable cassette may be used in the present invention. The cassette may include the disposable portions of the valves 6 and 7, the pump 4 and the air detector 5. The pump 4 and the air detector 5 may use the same chamber—specifically, a pressure-conduction chamber—to perform the air detection and the pumping. The valves and pressure-conduction chamber disclosed in U.S. Pat. No. 5,088,515, which is incorporated herein by reference, may be used as valves 6, 7 and/or 9, and for the air detector 5 and/or the pump 4. The body of the cassette is made of relatively rigid material, such as a thermoplastic, and one or several flexible membranes are disposed on the rigid body to form the membranes of the valves and the pressure-conduction chamber. The flexible tube portions of the IV line 3 and the return line 8 may be connected to the rigid portion of the cassette, so as to communicate with the fluid passageways within the cassette. The disposable cassette is placed into a control unit housing that can actuate the valves 7 and 8, and that can detect the presence of air and/or the amount of fluid in the pressure-conduction chamber.

Figure 4:
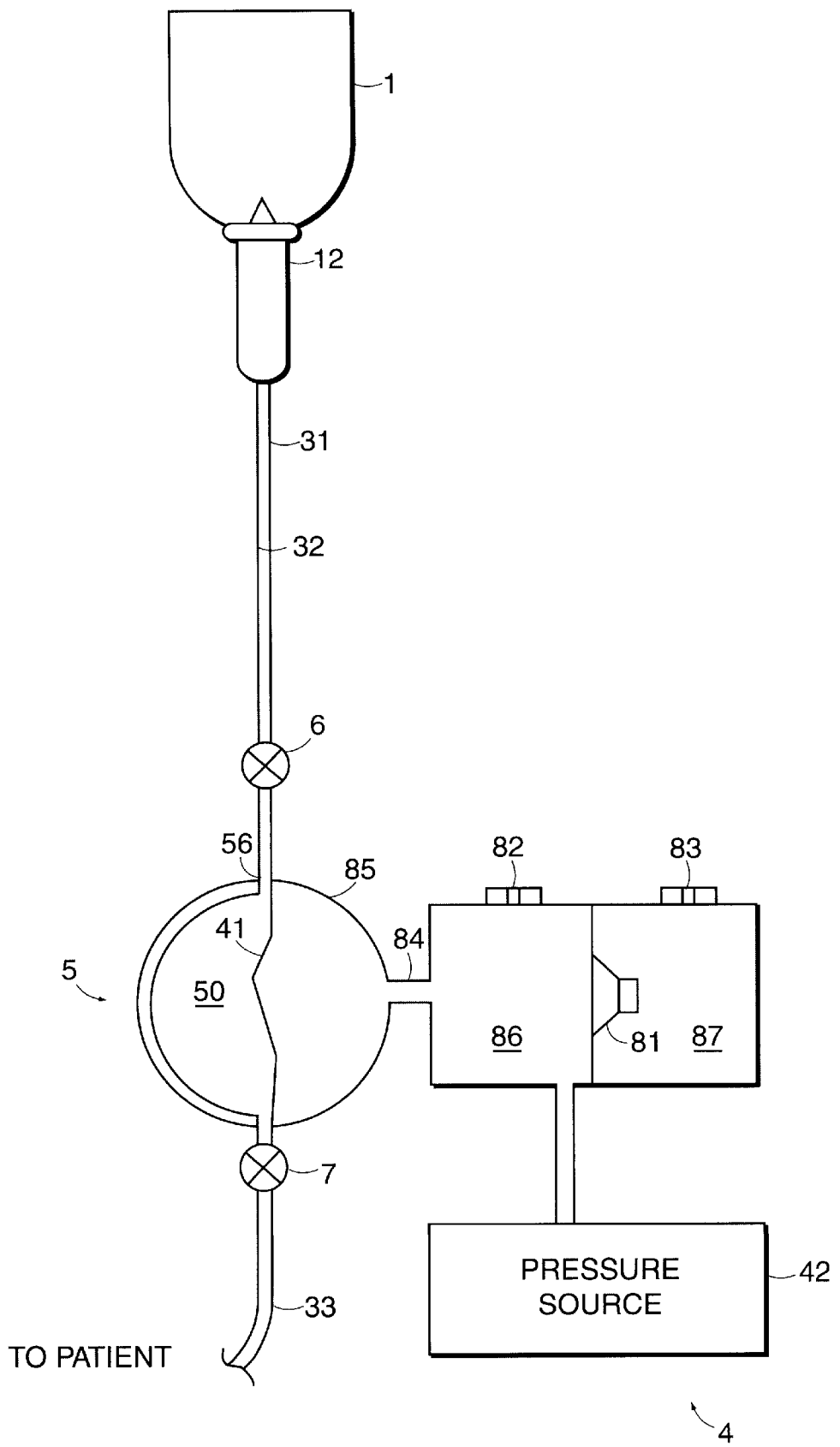
FIG. 4 shows a preferred embodiment of an air-elimination system according to the present invention.

FIG. 4 shows a preferred embodiment of the invention. In the FIG. 4 embodiment, a return line is not used, and the fluid containing the air is forced up the portion 31 of the IV line between the separation chamber—which is, in the depicted arrangement, the drip chamber 12—and the air detector 5. As noted above, the embodiments shown in FIGS. 1, 2 and 3 can force the fluid containing the air up through the IV line, by introducing additional fluid from below the air detector by the return line. In the FIG. 4 embodiment, the pressure-conduction chamber 50, where the air is detected, is able to hold a maximum volume of fluid that is greater than the volume of fluid contained in the lumen 32 of the IV line's upper portion 31. This arrangement permits all of the air that may be present in the IV fluid in the pressure-conduction chamber 50 to be forced up through the IV line's upper portion 31 to the drip chamber 12, or other separation chamber. This arrangement limits the length of the IV line's upper portion 31. If it is desired to have a longer upper portion 31 to the IV line, then the diameter of the upper portion's lumen 32 must be made smaller and/or the maximum volume of the pressure-conduction chamber must be increased. It is, however, undesirable to make the pressure-conduction chamber too large, because if it is too large the accuracy of the flow-rate measurements may be reduced.

As with the embodiments of FIGS. 1–3, the pressure-conduction chamber 50, along with the portions of the valves 6, 7 that come into contact with the IV fluid, are preferably located in a cassette, which is disposable along with the upper portion 31 and the lower portion 33 of the IV line. The rest of the hardware for detecting air is located in a control unit housing that receives and holds the cassette, and which does not come into direct contact with the IV fluid. The hardware preferably used to detect air bubbles in pressure-conduction chamber 50 is described in U.S. Pat. No. 5,349,852, or the above-referenced patent application Ser. No. 08/477,380 filed Jun. 7, 1995. A preferred embodiment of such an air-detection system uses a loudspeaker 81 mounted between two chambers 86, 87. The forward chamber 86 is connected to the cavity 85 that receives the pressure-conduction chamber 50 by a port 84 that is tuned for creating a resonance. The forward chamber 86 has a microphone 82 for detecting the resonance, and the rear chamber 87 has a microphone 83 for use in calibrating the air-detection system. This air-detection system can also function as a volume-measurement system, measuring the volume of the IV fluid in the pressure-conduction chamber 50 (as described for instance in U.S. Pat. No. 5,349,852), so that the flow rate to the patient can be monitored and controlled.

The pressure-conduction chamber 50 containing the IV fluid is separated from the air (or other gas) in the housing's cavity 85 by a fluid-impermeable membrane 41. By applying a pressure against this membrane 41, such as by a pressure source 42 through the forward chamber 86 and the port 84 of the air-detection system, the fluid can be forced out of the pressure-conduction chamber 50. If valve 6 is closed and valve 7 open, then the IV fluid is pumped towards the patient. If air (or at least a previously set amount of air) is detected in the pressure-conduction chamber 50, the control system causes outlet valve 7 to remain closed, opens inlet valve 6, and activates the pressure source 42 so as to force the fluid up through the upper portion 31 of the IV line.

Preferably, the pressure-conduction chamber 50 is held so that the port 56 leading from the inlet valve 6 is located at the upper end of the chamber 50 so that any air bubbles are likely to be located near the port 56 when the pumping arrangement is activated to force the bubble up to the drip chamber 12. Thus, when the pressure source 42 applies the pressure against the membrane 41, the bubble will immediately be forced all the way to the drip chamber 12. A membrane 41 having a structure that collapses asymmetrically, such as the membrane described in the above-referenced patent application Ser. No. 08/478,065 filed Jun. 7, 1995, may be used to obtain an uneven collapse of the membrane 41 when gas pressure is applied from the pressure source 42, wherein the collapse begins in the lower half of the membrane 41 so as to force the fluid and any bubbles in the bottom half of the chamber 50 to the top of the chamber, before the top portion of the membrane 50 collapses. When the top portion of the membrane collapses, the fluid remaining in the chamber 50 is forced up through the upper portion 31 of the IV line 3.

If the bubble is large enough, not all of the bubble may have been forced all the way to the drip chamber 12 after the pressure source 42 has forced all of the IV fluid out of the pressure conduction chamber 50. In such a situation, several iterations of the purging process may be required. Specifically, after the membrane 41 is forced to the left as far as it can go so that no more fluid (including both the IV fluid and the air) can be forced out of the pressure-conduction chamber 50, more IV fluid can be allowed to flow from the drip chamber 12 through the upper portion 31 of the IV line into the pressure-conduction chamber 50, in order to fill the pressure-conduction chamber to its maximum volume. A portion of the original air bubble or bubbles should have separated from this additional IV fluid in the drip chamber. This additional IV fluid can be allowed to flow to the pressure-conduction chamber 50 by force of gravity alone, or preferably the pressure source 42 (which can include a reciprocating piston, a pump, or positive- and negative-pressure sources) can provide a negative pressure to the membrane 41, so as to draw IV fluid into the pressure-conduction chamber 50 more quickly. The size of the air bubble should now be much smaller. If it is large enough to have a fault-condition signal generated by the air detection system, valve 6 will be opened, and a positive pressure reapplied to the membrane 41 by the pressure source 42. What is left of the bubble is then forced up the IV line's upper portion 31, and some or all of the bubble should enter the drip chamber and separate from the IV fluid. If a portion of the bubble still remains in the pressure-conduction chamber 50 after it is again refilled, the purging process is repeated.

Figure 5:
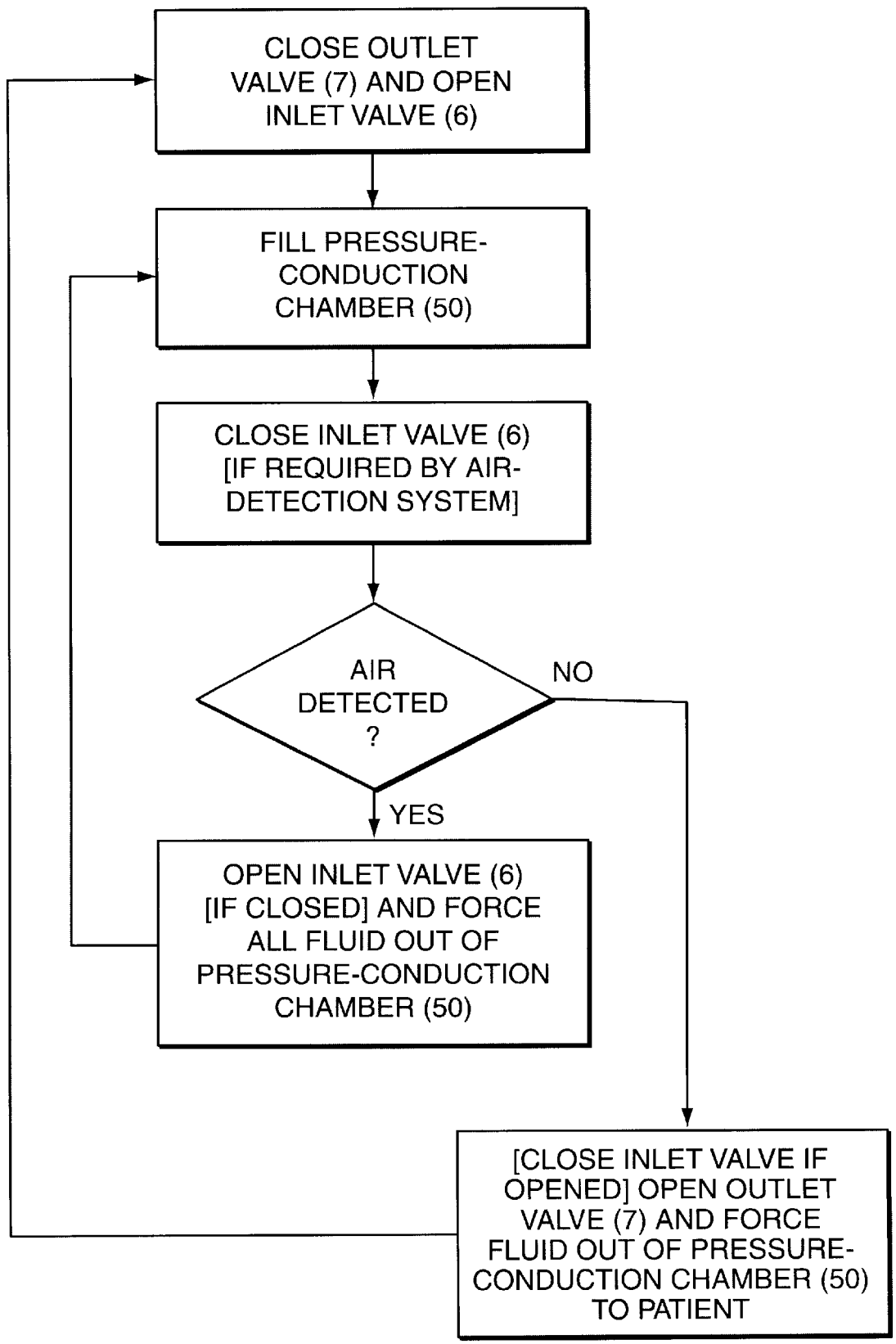
FIG. 5 is a flow chart depicting a preferred method of carrying out the invention.

The foregoing process is represented in the flowchart of FIG. 5. This process shows how air may be routinely purged from the IV fluid before reaching the patient and without requiring the intervention of any medical personnel. Although it is preferred to use the pumping mechanism (e.g., a peristaltic pump, or a pressure source 42 acting on the membrane 41 as shown in FIG. 4), to draw fluid into the chamber 50 from the fluid source 1 or to force fluid to the patient, gravity may be used instead. Additional steps may be added to the process—after no air is detected and before the outlet valve 7 is opened, and then after the outlet valve 7 is closed and before the inlet valve 6 is opened—in order to measure the amount of fluid dispensed to the patient.

The present invention is useful for re-priming an IV line after an IV source 1 has emptied and been replaced. Frequently, in such situations the whole upper portion 31 of the IV line may be filled with air. (With the present invention, the air-detection system should have kept the IV line's lower portion 33 filled with IV fluid.) Once the new IV source 1 is provided, air in the pressure-conduction chamber 50 is forced up through IV line's upper portion 31. IV fluid from the source 1 should be present in the drip chamber 12, so that when the system draws fluid down to the pressure-conduction chamber, at least some of that fluid should be IV fluid. The air and the IV fluid are then forced out of the pressure-conduction chamber 50 again—with the air being forced out first since the liquid should have fallen to the bottom of the pressure-conduction chamber 50. Once again, fluid is drawn into the pressure-conduction chamber 50, and since the air should have separated from the liquid in the drip chamber 12, more IV fluid should be drawn into the pressure-conduction chamber 50 than before. These steps are repeated until the air detector senses that the pressure-conduction chamber 50 is filled with IV fluid without any air bubbles (or until the amount of air is sufficiently low).

In the situation where the air bubble is not located near the inlet port 56 but instead is sticking to the membrane 41 or the wall of the pressure-conduction chamber 50, several repetitions of forcing fluid up and down the IV line's upper portion 31 will usually dislodge the bubble, thereby allowing the bubble to float up towards the inlet port 56 which should be at the top of the pressure-conduction chamber. Once the bubble moves near the inlet port 56, it should be forced out of the pressure-conduction chamber 50 with the next purge of fluid up the IV line's upper portion 31.

Figure 6:
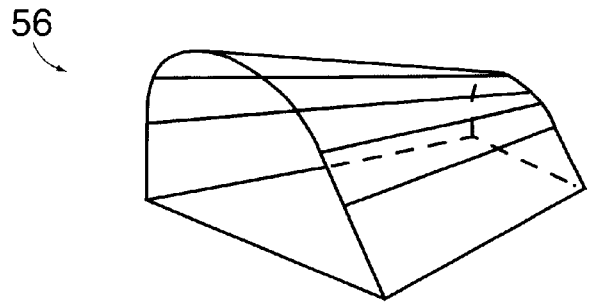
FIG. 6 shows a perspective view of a preferred shape for an inlet port to a pressure-conduction chamber, which may be used with the present invention.
Figure 7:
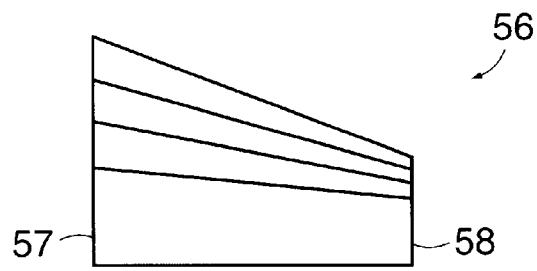
FIG. 7 shows a side view of the inlet-port shape shown in FIG. 6.
Figure 8:
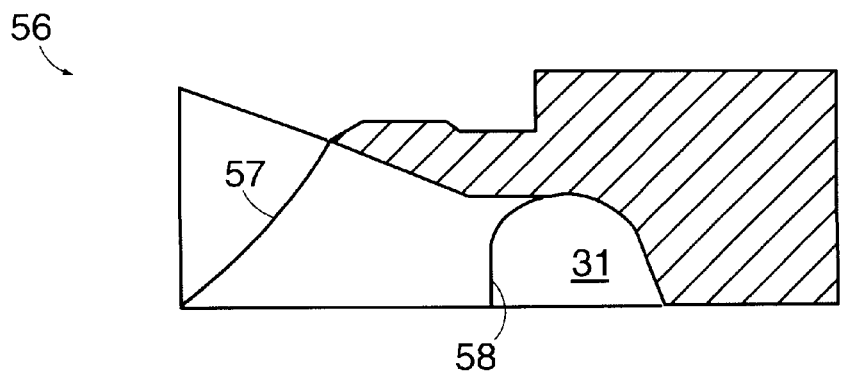
FIG. 8 shows a cross-section of the inlet port the shape of which is depicted in FIGS. 6 and 7.

Preferably, the inlet port 56 is shaped so that a small bubble will not tend to stick to an edge of the port while allowing liquid to flow past it. If the bubble is large, it is likely that at least a portion of it will be forced up through the IV line's upper portion 31, regardless of the port's shape; a small bubble, however, may be more difficult to dislodge. (Small bubbles are less of a concern than large bubbles, so the air-detection system may be calibrated to ignore bubbles that are small enough.) To prevent such sticking of a small bubble, the port 56 preferably flares out so that the corner where the port 56 meets the inner wall of the pressure-conduction chamber 50 is greater than 90°, making the corner less likely a place where the bubble will stick. However, the mouth of the port 56 cannot be so large that liquid can easily flow by the bubble when fluid is exiting the pressure-conduction through the port 56. In order to accomplish this, the port must be sized and shaped so that the surface tension of the IV fluid being forced upward from the pressure-conduction chamber 50 forces a bubble located at the port 56 up through the inlet valve 6. It is also preferable that the port 56 be sized and shaped so that when liquid is pulled back into the pressure-conduction chamber 50, the bubble can hover near the port as liquid passes around it. A preferred inlet port 56 shape is shown in FIGS. 6 and 7. The port's size increases from the end 57 that connects to the IV line's upper portion 31 to the end 58 leading into the pressure-conduction chamber. FIG. 8 shows a cross-section of the inlet valve 56. Since the pressure-conduction chamber is preferably curved—and preferably generally hemispherical—in order to make it easier for the pressure-conduction chamber's membrane (item 41 in FIG. 4) to force as much fluid as possible out of the pressure-conduction chamber, the mouth at the chamber end 57 of the port 56 is curved. It has been found that providing an inlet port to the pressure-conduction chamber with this shape improves the air-elimination system's ability to purge bubbles from the chamber.

The control unit, of course, requires a power supply to supply the power necessary to detect and eliminate air bubbles. Prior-art pumping units used heavy-duty cords to attach to an AC power outlet, and they also included an internal battery so that when the unit was unplugged from the AC outlet the unit could continue to function Prior-art pumping units also included the ability to daisy-chain—that is, to plug into a neighboring unit, which was attached to either an AC outlet or to yet another unit, and at some point the chain was connected to an AC outlet. Daisy-chaining the AC power was convenient, since it was often necessary to mount several pumping units to the same IV pole to control the flow through several IV lines to the same patient.

Figure 9:
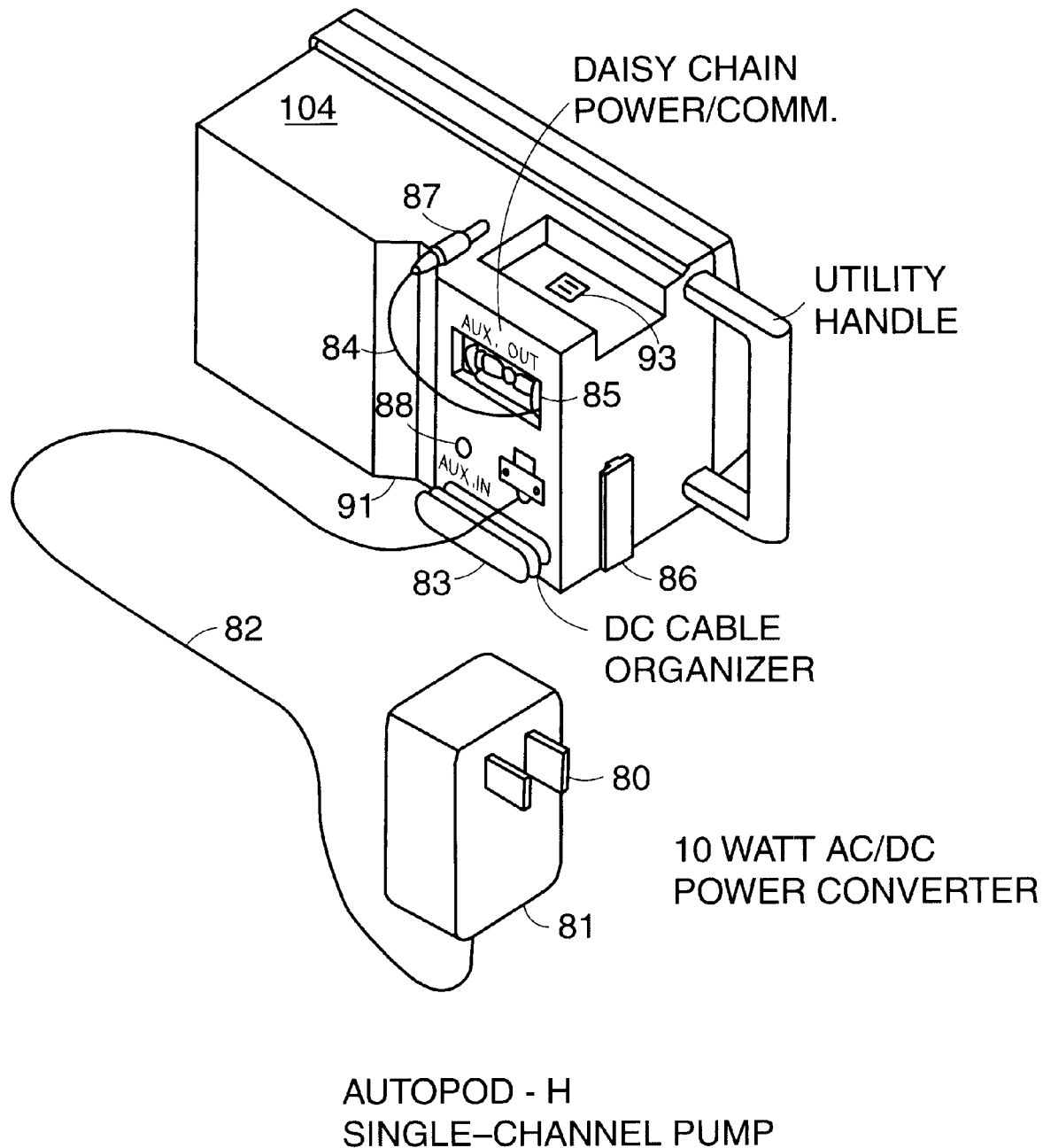
FIG. 9 shows a rear perspective view of a control unit according to a preferred embodiment of the invention.

FIG. 9 shows a preferred, novel power supply system for the control unit of the present invention. In a preferred embodiment, the control unit is one as described in the above-referenced patent application Ser. No. 08/472,212. Instead of using a heavy-duty AC power cord, the unit uses a wall plug-in AC-DC adapter 81, which has prongs for connecting to the AC outlet. The adapter 81, which includes a step-down transformer, is connected to the unit's housing 104 by a thin DC cord 82, thereby avoiding the use of the bulky AC power cords. The unit also includes a second DC cord 84 with a DC plug 87 for providing power to a second unit. Both cords 82, 84 include organizers 83, 85, to hold the cord when it is not being used. Attachment means 86 are also included on the housing 104 for holding the adapter 81 when it is not in use. The control unit also includes a receptacle 88 for receiving a DC plug, and DC power from another unit. An internal battery is located inside the housing 104, so that the unit may work even if its adapter 81 is not connected to a wall outlet, and its receptacle 88 not connected to another unit. Although the internal battery is recharged whenever the unit is connected to a wall outlet, either directly or through another unit, the internal battery can run down. In order to provide emergency power in such a situation when an AC outlet is not convenient, the unit further includes a receptacle 93 for an external battery pack. In one preferred method of using the unit, an external battery pack is kept attached to receptacle 93, and the internal battery is only used in emergencies. When the external battery pack runs down, and no AC outlet is conveniently available, the external battery pack may be removed and replaced by a fully charged battery pack; the internal battery pack provides the interim power while the external battery packs are being switched.

Figure 10:
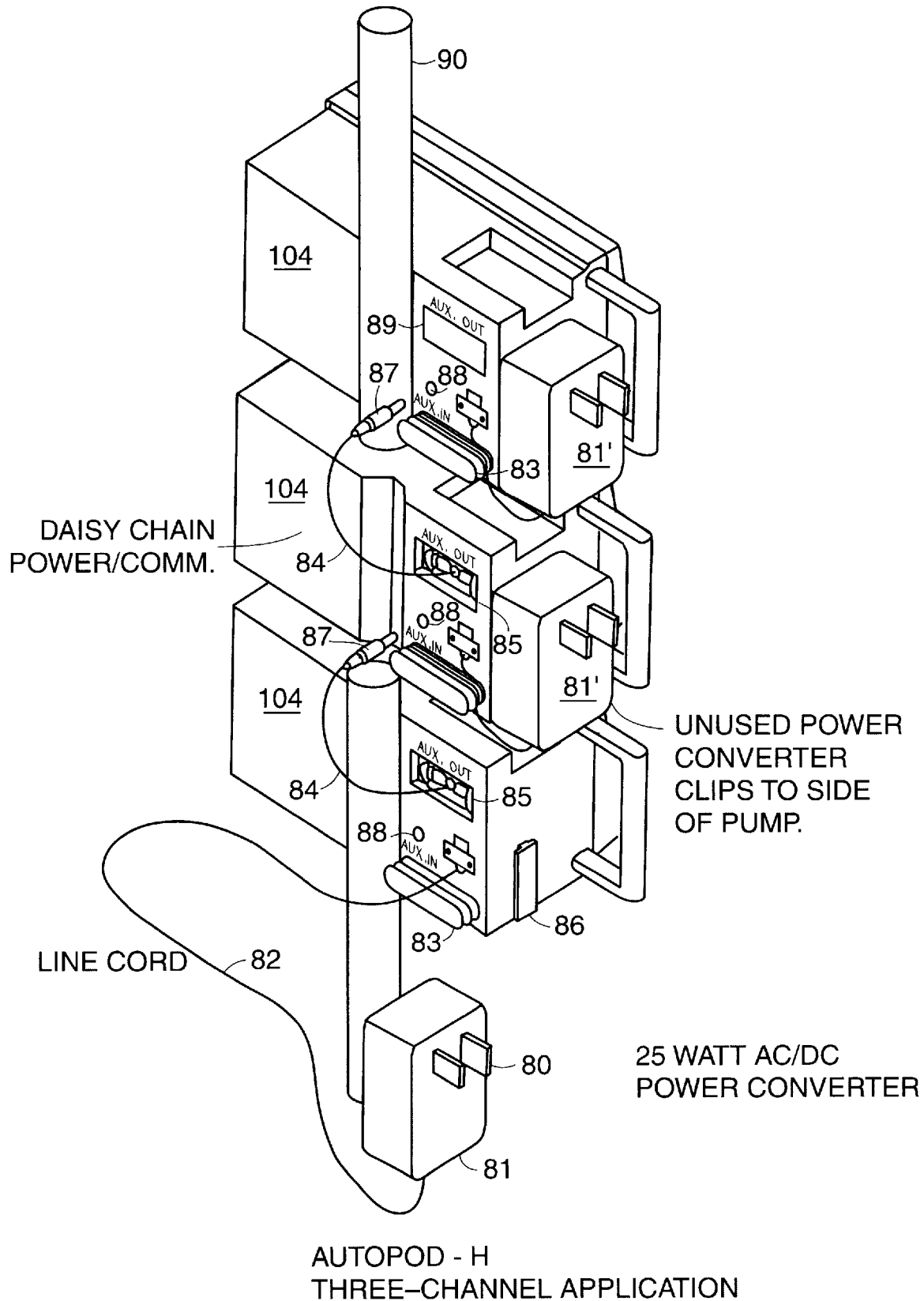
FIG. 10 shows a plurality of control units of the type shown in FIG. 9 mounted on a IV pole.

The back of the unit's housing 104 includes pole-grasping means 91, so that the unit may be mounted on an IV pole. FIG. 10 shows three units mounted to an IV pole 90. The bottom unit obtains its power through cord 82 from its adapter 81, which is plugged into an AC outlet. By plugging the bottom unit's DC plug 87 into the middle unit's receptacle 88, the second cord 84 of the bottom unit provides power to the middle unit. Likewise, by plugging the middle unit's DC plug 87 into the top unit's receptacle 88, the cord 84 of the middle unit provides power to the top unit. Since the DC plug of the top unit is not used, it and its cord may be stored on an organizer, which may be hidden under a panel 89. The adapters 81' of the middle and top units are not used and are therefore stored on the side of the housing 104, which has attachment means similar to the attachment means 86 on the bottom unit Other forms of attachment means 86 may be used, such as the fastening means commonly sold under the trademark "Velcro." Other forms of organizers 83, 85 may also be used, such as spring-loaded coiling systems, which can automatically retract a cord inside the housing 104 so as to leave only the adapter 81 or the DC plug 87 visible.

The daisy-chain cords 84 may include additional wires to permit the communication of information between he units. This feature is important if the patient requires a drug therapy where the multiple medications or other fluids should be given in a particular sequence. This feature is also useful if medical personnel wish to download all the information about the IV fluid delivered to the patient, e.g. amount and time of each fluid; this downloading may be accomplished by accessing a single unit, which has access to the information in the other units, instead of having to access each unit separately. This feature is also useful for providing software code to multiple units at the same time, such as when a new drug-delivery protocol is to be programmed into the units, or even at the factory for loading software into several units at the same time.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. An air-elimination system, for a fluid delivery system for injection of intravenous fluid into a patient, comprising:

separation means for permitting the separation of air from the intravenous fluid;

an intravenous line in fluid communication with the separation means;

air-detection means, disposed in the intravenous line, for detecting air in the fluid and emitting a fault-condition signal, the intravenous line having a first portion between the separation means and the air-detection means, and a second portion between the air-detection means and the patient;

valve means, disposed in the intravenous line's second portion, for permitting or preventing flow to the patient;

pump means for urging fluid towards the separation means upon activation; and control means, in communication with the air-detection means, for (i) setting the valve means to prevent flow to the patient and activating the pump means, so as to move the fluid containing air from the air-detection means to the separation means, in response to a fault-condition signal, and otherwise (ii) setting the valve means to permit flow to the patient.

2. A system according to claim 1, wherein the pump means includes a pump disposed in the intravenous line upstream from the valve means.

3. A system according to claim 2, wherein the pump means includes a chamber disposed in the intravenous line, wherein pressure may be applied to the fluid in the chamber.

4. A method for eliminating air from an intravenous fluid delivery system, comprising the steps of:

providing a separation chamber where air may separate from the fluid;

providing an intravenous line downstream of the separation chamber;

providing an air detector in the intravenous line;

providing a pump in the intravenous line;

providing a valve in the intravenous line downstream of the pump and the air detector;

using the air detector to detect air in the fluid;

generating a signal when a specified amount of air is detected in the fluid;

closing the valve in response to the signal;

using the pump to urge fluid upstream through the intravenous line to the separation chamber in response to the signal.

5. A chamber for the removal of air bubbles in a liquid, the chamber comprising:

a rigid portion defining part of the chamber;

a flexible portion connected to the rigid portion and further defining the chamber such that, when external pressure is applied to the flexible portion, the flexible portion collapses toward the rigid portion forcing the liquid out of the chamber; and a port defined by the rigid portion and located at the upper end of the chamber, the port increasing in cross-sectional area nearer the chamber so as to reduce the likelihood that a bubble will stick to an edge of the port;

wherein the port is shaped and sized so that, when the liquid is forced out from the chamber through the port, the liquid's surface tension forces a bubble located at the port through the port without allowing the liquid to flow by the bubble easily.

6. A control unit for receiving a cassette mounted in an intravenous line, the control unit comprising:

a housing;

means, located on the housing, for receiving and actuating the cassette;

means, located on the housing, for mounting the control unit to a pole, such that a plurality of control units may be mounted one above the other on the same pole, in order to control several intravenous lines leading to a patient;

AC means for receiving AC power from a wall outlet and converting the AC power to DC power, the AC means being connected to the control unit housing by a first cord for carrying DC power; and DC means for receiving DC power from a second control unit mounted on the same pole, wherein the second control unit is connected to a wall outlet, wherein the DC means receives the DC power through a second cord for carrying DC power.

7. A control unit according to claim 6, wherein the second cord includes wires for carrying electrical signals between control units.

8. A control unit for receiving a cassette mounted in an intravenous line, the control unit comprising:

a housing;

means, located on the housing, for receiving and actuating the cassette;

means, located on the housing, for mounting the control unit to a pole;

AC means for receiving AC power from a wall outlet and converting the AC power to DC power;

internal-battery means for providing DC power when the AC means is disconnected from the wall outlet, the internal battery means being located inside the housing; and external-battery-receiving means for permitting an external battery pack to be connected to the housing's exterior to provide power to the control unit in lieu of AC power from a wall outlet and from the internal-battery means.

* * * * *